(12) United States Patent
Kim

(10) Patent No.: US 7,998,077 B2
(45) Date of Patent: Aug. 16, 2011

(54) DEVICE FOR ROTATING A TRANSDUCER OF AN ULTRASONIC PROBE

(75) Inventor: Seong Rae Kim, Seoul (KR)

(73) Assignee: Medison Co., Ltd., Kangwon-do (KR)

( * ) Notice: Subject to any disclaimer, the term of this patent is extended or adjusted under 35 U.S.C. 154(b) by 732 days.

(21) Appl. No.: 11/964,876

(22) Filed: Dec. 27, 2007

(65) Prior Publication Data

US 2008/0161694 A1    Jul. 3, 2008

(30) Foreign Application Priority Data

Dec. 27, 2006 (KR) .................. 10-2006-0135164

(51) Int. Cl.
*A61B 8/14* (2006.01)

(52) U.S. Cl. .................. 600/459; 600/407; 600/437

(58) Field of Classification Search .................. 600/407, 600/437
See application file for complete search history.

(56) References Cited

U.S. PATENT DOCUMENTS

| | | | | |
|---|---|---|---|---|
| 4,203,324 A | * | 5/1980 | Baumoel | 73/290 V |
| 5,048,529 A | | 9/1991 | Blumenthal | |
| 5,351,692 A | * | 10/1994 | Dow et al. | 600/463 |
| 5,833,616 A | | 11/1998 | Gruner et al. | |
| 2006/0017330 A1 | | 1/2006 | Botos et al. | |

FOREIGN PATENT DOCUMENTS

| | | |
|---|---|---|
| EP | 1 576 926 A1 | 9/2005 |
| EP | 1 676 531 A1 | 7/2006 |
| EP | 1 744 178 A2 | 1/2007 |
| KR | 10-2005-0086646 | 8/2005 |
| KR | 2006-0076026 | 7/2006 |

* cited by examiner

*Primary Examiner* — Tse Chen
*Assistant Examiner* — Joel F Brutus
(74) *Attorney, Agent, or Firm* — McDermott Will & Emery LLP

(57) ABSTRACT

Embodiments of the present invention may provide a device for rotating a transducer of an ultrasonic probe, which has a simple manufacturing process and a small size. The device may comprise: a drive motor; a pulley rotatably driven by the drive motor; wire-ropes wound around the pulley; a rotatable transducer having a plurality of ultrasonic elements; and buffer springs connecting one ends of the wire-ropes and the transducer, the buffer springs being attached to the transducer.

3 Claims, 9 Drawing Sheets

DEVICE FOR ROTATING A TRANSDUCER OF AN ULTRASONIC PROBE

The present application claims priority from Korean Patent Application No. 10-2006-0135164 filed on Dec. 27, 2006, the entire subject matter of which is incorporated herein by reference.

BACKGROUND

1. Field

The present invention generally relates to a device for rotating a transducer provided in an ultrasonic probe for use with an ultrasonic diagnostic apparatus.

2. Background

An ultrasonic diagnostic apparatus is widely used to diagnose a subject by visualizing a portion of the subject's body. For example, the ultrasonic diagnostic apparatus diagnoses a subject by detecting alien substances of organs, measuring the level of a lesion, or observing a tumor or a fetus. Such an ultrasonic diagnostic apparatus generally employs various ultrasonic probes to obtain information on a subject's body. The ultrasonic probe has a transducer, which emits ultrasonic waves into an inspection portion of a subject and receives the reflected ultrasonic waves therefrom to convert the reflected ultrasonic waves into electric signals. The ultrasonic diagnostic apparatus processes the electric signals from the ultrasonic probe, thereby forming ultrasonic images that show the inspection portion of the subject's body. In the recent years, an ultrasonic probe configured to rotate the transducer is used to obtain more accurate or three-dimensional ultrasonic images.

One example of a prior art ultrasonic probe for obtaining a three-dimensional image is described in Korean Patent Publication No. 10-2006-76026 (published on Jul. 4, 2006).

Hereinafter, the prior art device for rotating the transducer of an ultrasonic probe for obtaining a three-dimensional image will be described with reference to FIGS. 1 to 4.

As shown in FIGS. 1 and 2, the prior art device for rotating the transducer of an ultrasonic probe includes the following: a step motor 110 having a rotating shaft; a drive pulley 120 coupled to the rotating shaft of the step motor 110; a driven pulley 140; a belt 130 transmitting the drive force from the drive pulley 120 to the driven pulley 140; a driven shaft 141 coupled to the driven pulley 140; a wire-rope holder 150 coupled to the driven shaft 141; a transducer 170 having a rotating shaft 174; and a pair of wire-ropes with one ends fixed to the wire-rope holder 150 and other ends coupled to the transducer 170 for rotating the transducer 170 by drive force from the step motor 110.

As shown in FIG. 4, the wire-rope holder 150 has a buffer spring 151, both ends of which can be deformed as 151a or 151b by means of a tension force of the wire-rope 160.

Referring to FIGS. 3 and 4, the wire-rope 160 is knotted at an end of the buffer spring 151. The wire-rope 160 has a coupler 162 at the other end. The transducer 170 includes a wire-rope guide 172 having a slit 173. The wire-rope 160 is inserted into the slit 173 and the coupler 162 is fixed to the slit 173.

Thus, if the step motor 110 rotates the drive pulley 120, then the drive pulley 120 rotates the driven pulley 140 and the driven shaft 141. Then, the wire-rope holder 150 coupled to the driven shaft 141 is rotated. The rotation of the wire-rope holder 150 forms a tension to one of the wire-ropes for rotating the transducer 170.

The step motor 110 rotates to the right and reverses repeatedly. The wire-rope holder 150 has a means for buffering the shock by means of the repetitive right and reversal revolution of the step motor 110. The wire-rope holder 150 has many parts. Thus, there is a problem with the prior art device for rotating the transducer of an ultrasonic probe since the manufacturing process of such a device is quite complex.

Further, the driven shaft occupies a large area in the probe case. Accordingly, there is a further problem with the prior art device in that the total size of an ultrasonic probe may be quite large.

Consequently, there is a need to provide a device for rotating the transducer of an ultrasonic probe, which has a simple manufacturing process as well as a small size.

BRIEF DESCRIPTION OF THE DRAWINGS

Arrangements and embodiments may be described in detail with reference to the following drawings in which like reference numerals refer to like elements and wherein.

DETAILED DESCRIPTION OF THE PRESENT INVENTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Hereinafter, a device for rotating a transducer of an ultrasonic probe, which is constructed in accordance with an embodiment of the present invention, will be described in detail with reference to FIGS. 5 to 9.

Figure 1:
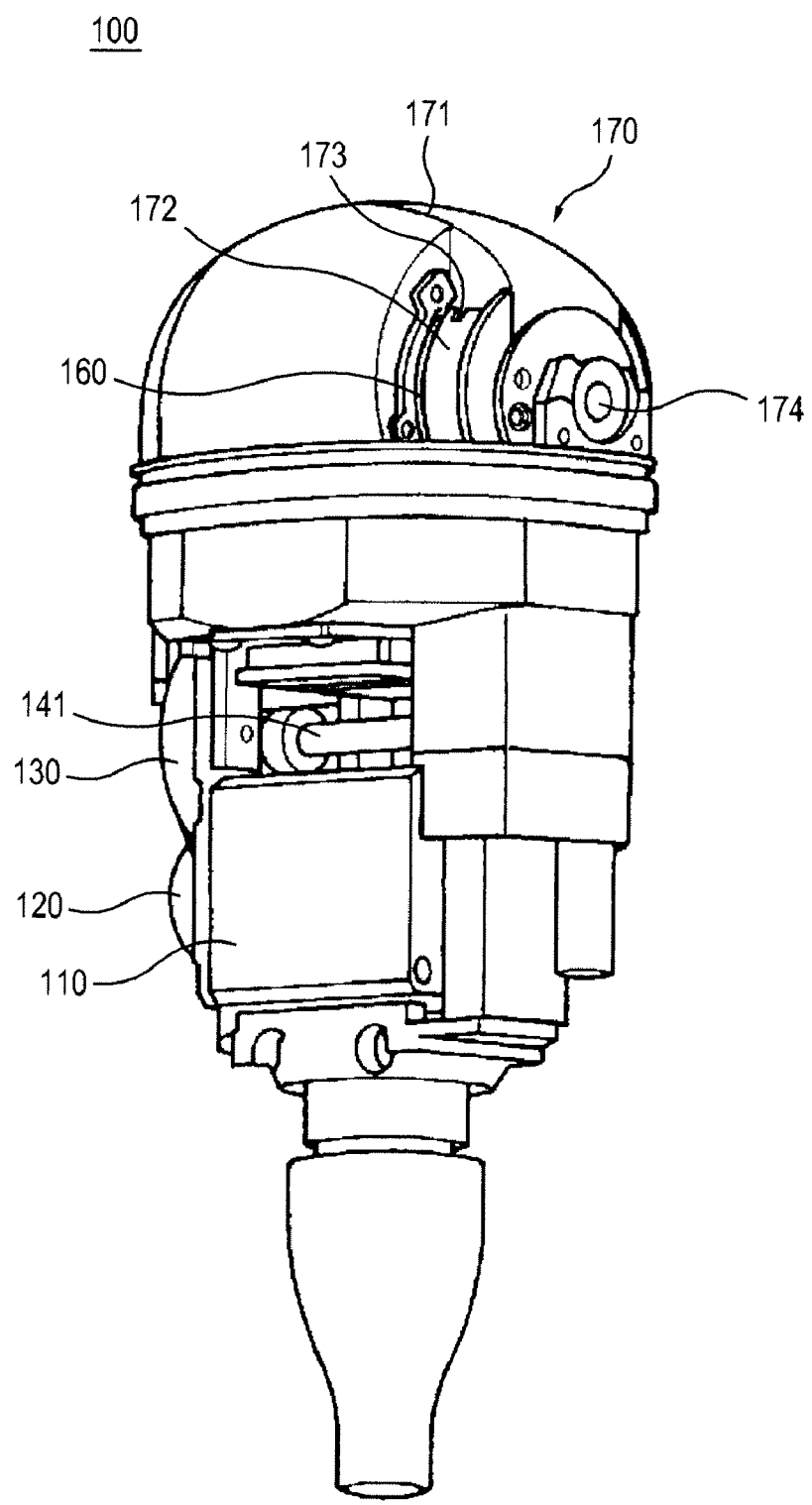
FIG. 1 is a perspective view showing an internal structure of a prior art ultrasonic probe for three-dimensional imaging.
Figure 2:
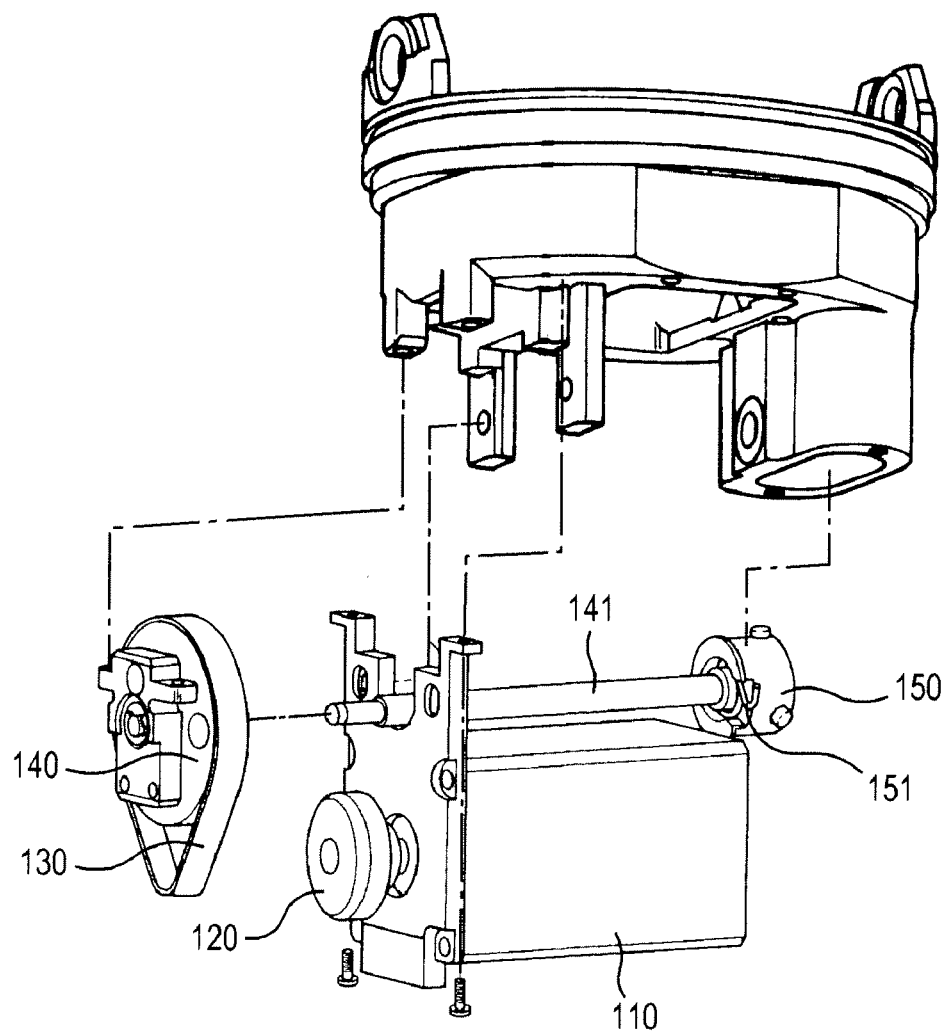
FIG. 2 is an exploded view of the ultrasonic probe shown in FIG. 1.
Figure 3:
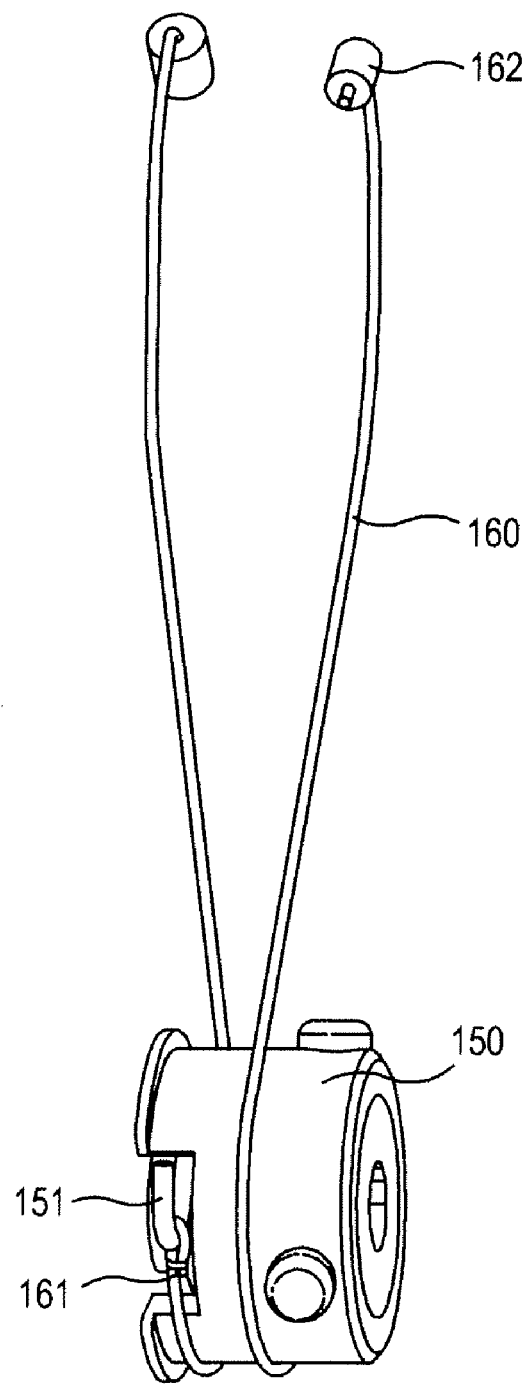
FIG. 3 is a perspective view of a wire-rope holder of the ultrasonic probe shown in FIG. 1.
Figure 4:
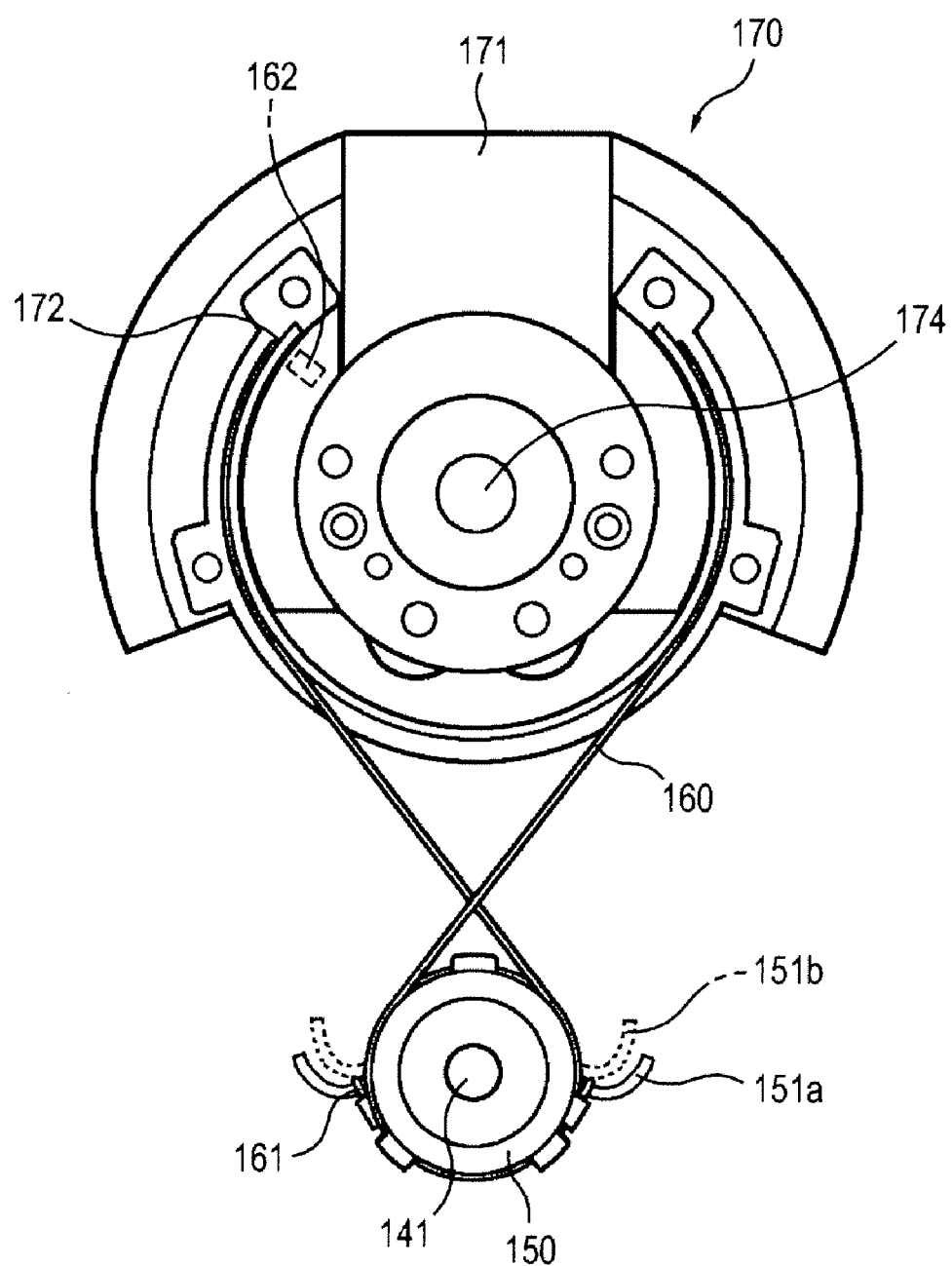
FIG. 4 is a side view of a transducer and the wire-rope holder of the ultrasonic probe shown in FIG. 1.
Figure 5:
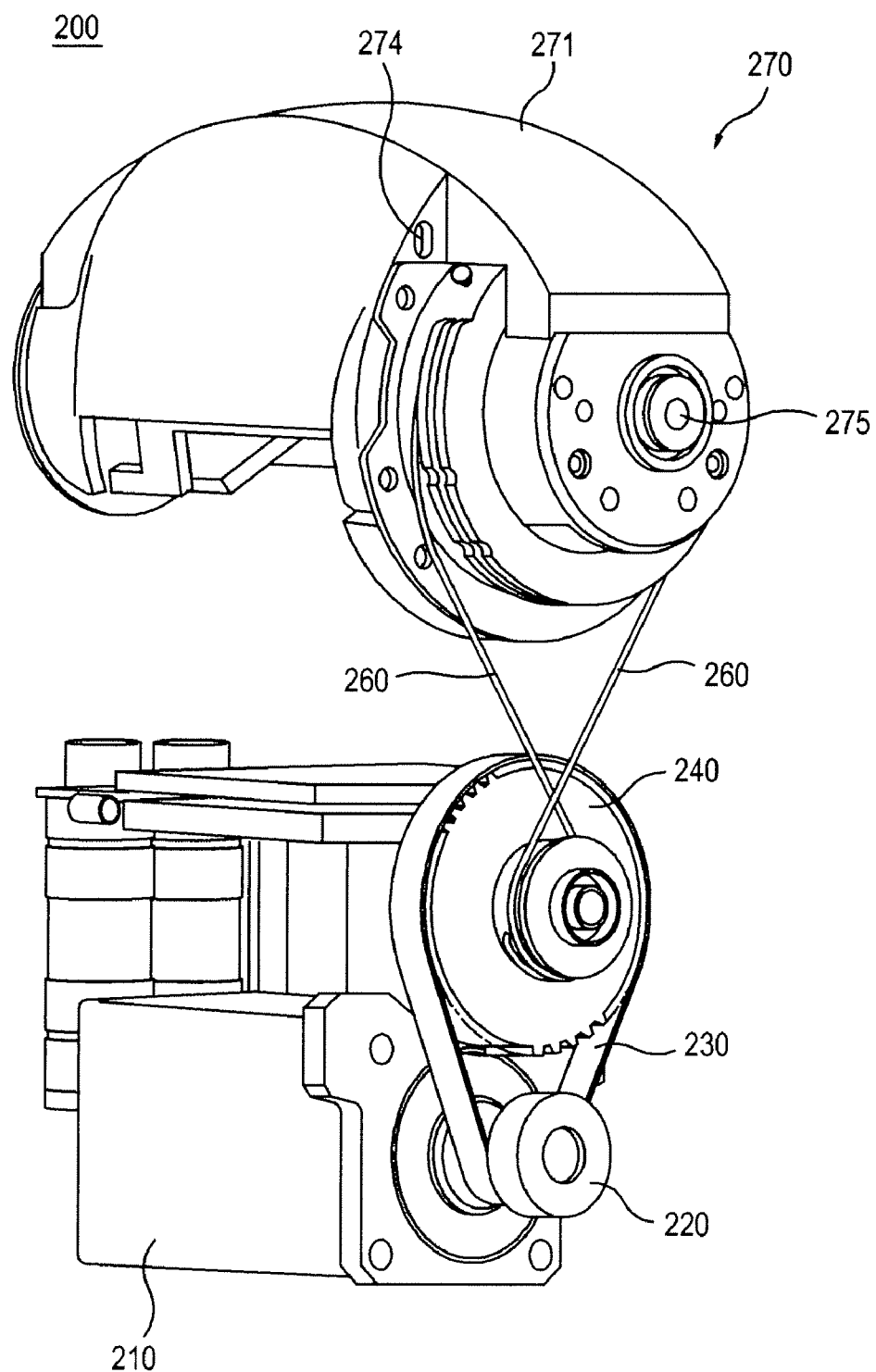
FIG. 5 is a perspective view showing an internal structure of an ultrasonic probe for three-dimensional imaging, which is constructed in accordance with an embodiment of the present invention.
Figure 6:
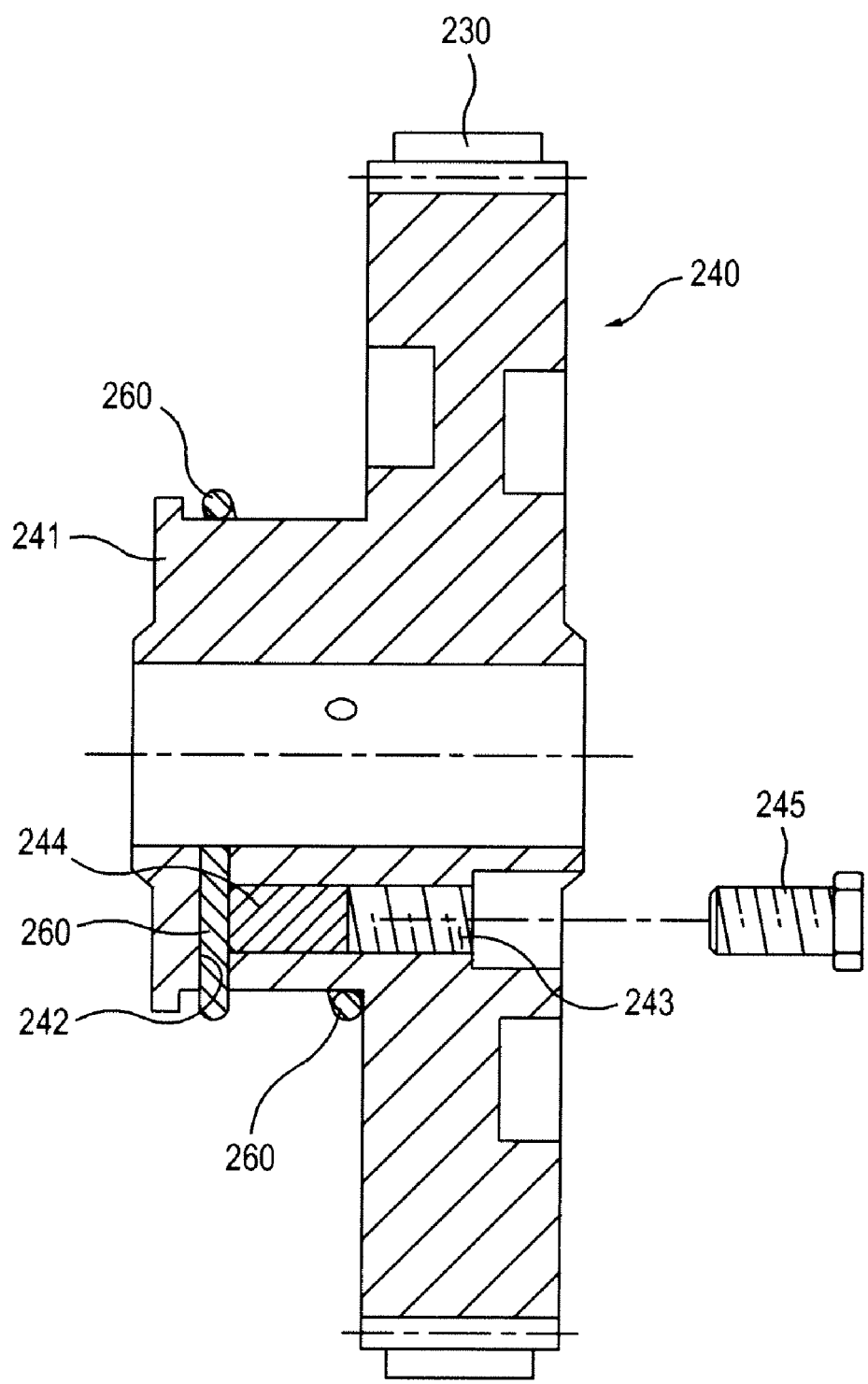
FIG. 6 is a cross-sectional view of a wire-rope holder of the ultrasonic probe shown in FIG. 5.

As shown in FIGS. 5 and 6, the device 200 for rotating a transducer of an ultrasonic probe includes the following: a drive motor 210 having a drive shaft; a drive pulley 220 coupled to the drive shaft of the drive motor 210; a driven pulley 240 driven by the drive pulley 220; a belt 230 transmitting a drive force from the drive pulley 220 to the driven pulley 240; and a transducer 270 connected to the driven pulley 240 via a pair of wire-ropes 260. A tension of the wire-rope 260 produced by the rotation of the driven pulley 240 can rotate the transducer 270. It is preferable that the drive motor 210 is a step motor.

A wire-rope holder 241 is formed on the driven pulley 240 concentrically, with one end of a wire-rope 260 being fixed to the wire-rope holder 241. The wire-rope 260 is wound around the wire-rope holder 241.

As shown in FIG. 6, a via hole 242 is formed on the wire-rope holder 241 from the periphery to the center. A screw hole 243 is formed on the driven pulley 240 orthogonal to the via hole 242. The screw hole 241 communicates a surface of the driven pulley 240 and the via hole 242.

One end of a wire-rope 260 is fixed to the wire-rope holder 240 such that one end of the wire-rope 260 is inserted to the via hole 242. The wire-rope is would around the wire-rope holder 241. A screw 245 is fastened in the screw hole 243 to press the wire-rope 260 inserted in the via hole 242. A pressing member 244 can be provided in the screw hole. The pressing member 244 is pressed by the screw 245, while the pressing member 244 presses the wire-rope 260 in the via hole 242. The pressing member 244 has a larger cross-sectional area and a smaller hardness than the screw 245 for protecting the wire-rope 260.

Figure 7:
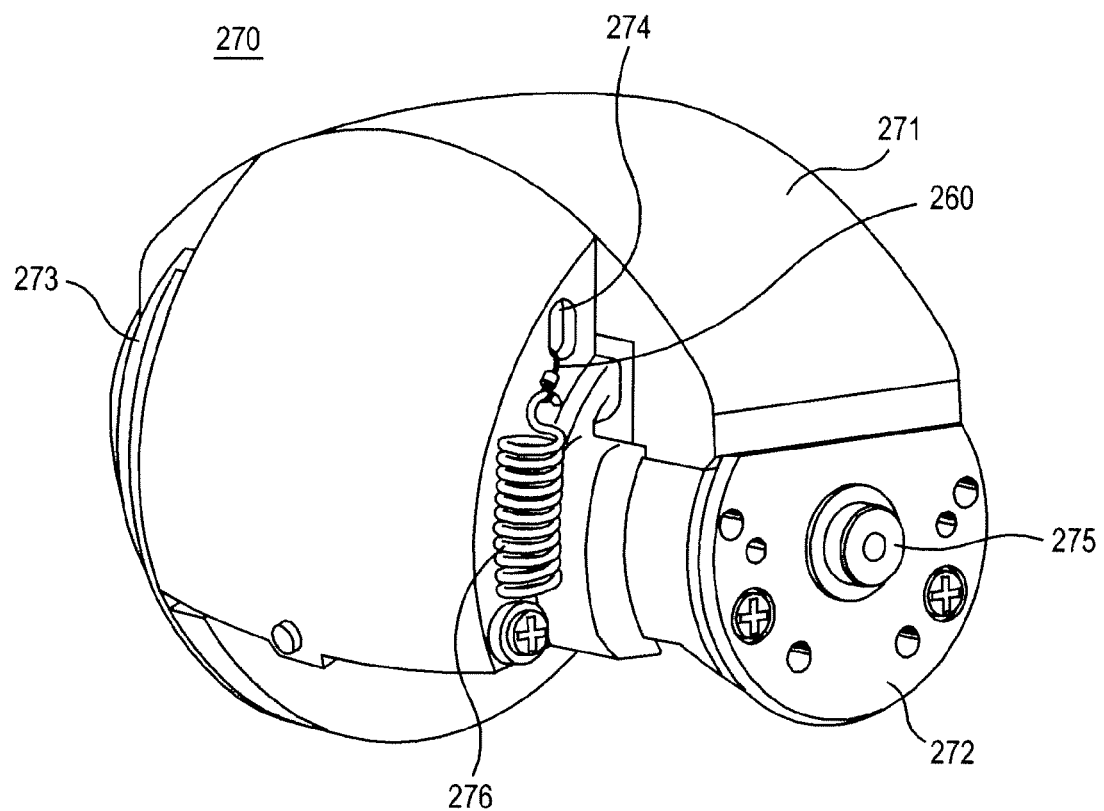
FIGS. 7 and 8 are perspective views of a transducer of the ultrasonic probe shown in FIG. 5.
Figure 8:
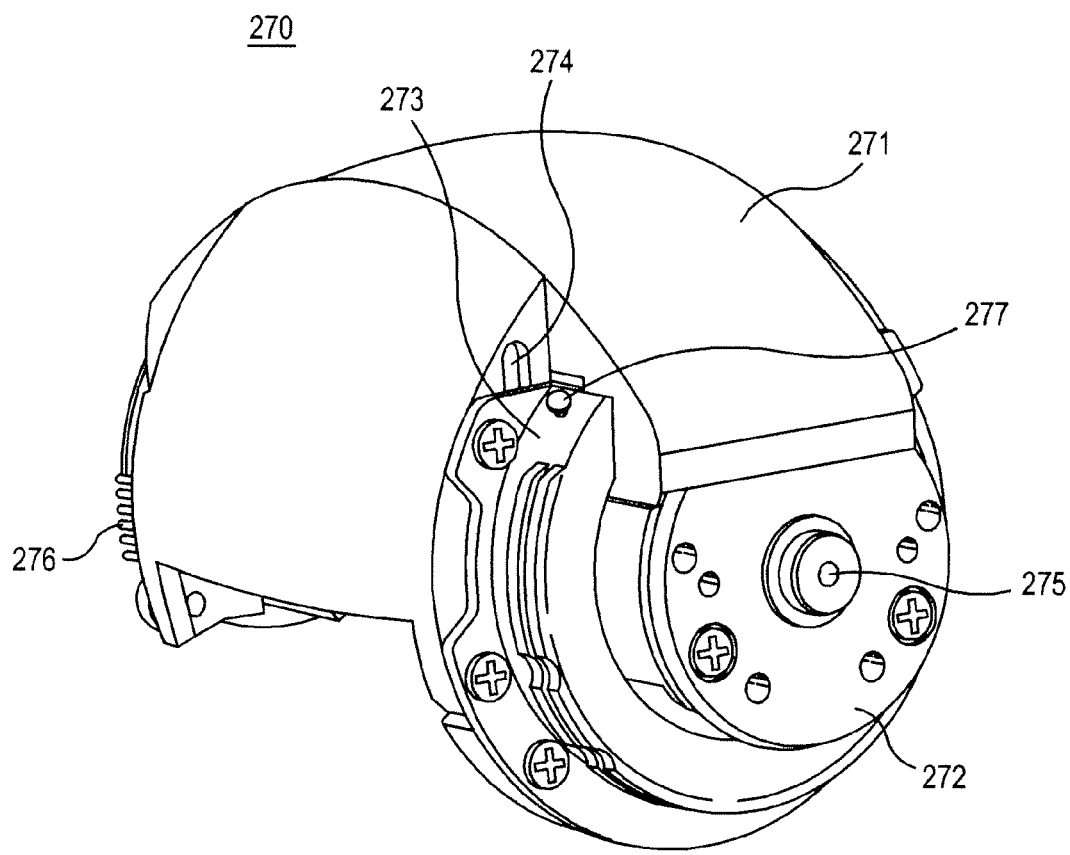

As shown in FIGS. 7 and 8, the transducer 270 includes: ultrasonic elements 271; a transducer holder 272 having a rotating shaft 275; a pair of wire-rope guides 273 mounted on both sides of the transducer 272 for arranging wire ropes 260 along the both sides of the transducer 270; a pair of wire-rope holes 274 formed through the transducer 270 parallel to the rotating shaft 275; and a pair of buffer springs 276 mounted on both sides of the transducer 270. Both buffer springs 276 are facial to each other around the transducer. Both wire-rope guides 273 are provided at both sides of the transducer 270. A vi a hole communicates an end of a wire-rope guide 273 and a corresponding buffer spring 276.

One end of the wire-rope 260 is fixed to the wire rope holder 240 and the other end thereof is fixed to one of the buffer springs 270 via the wire-rope guide 273 and the wire-rope hole 274. The wire ropes 260 are connected to the corresponding buffer springs 276.

A pair of pin guides 277 having a cylindrical cross-section are formed adjacent to the end of the wire-rope holes 274. This is so that the edges of the wire-rope holes 274 do not contact the wire-ropes 260.

Figure 9:
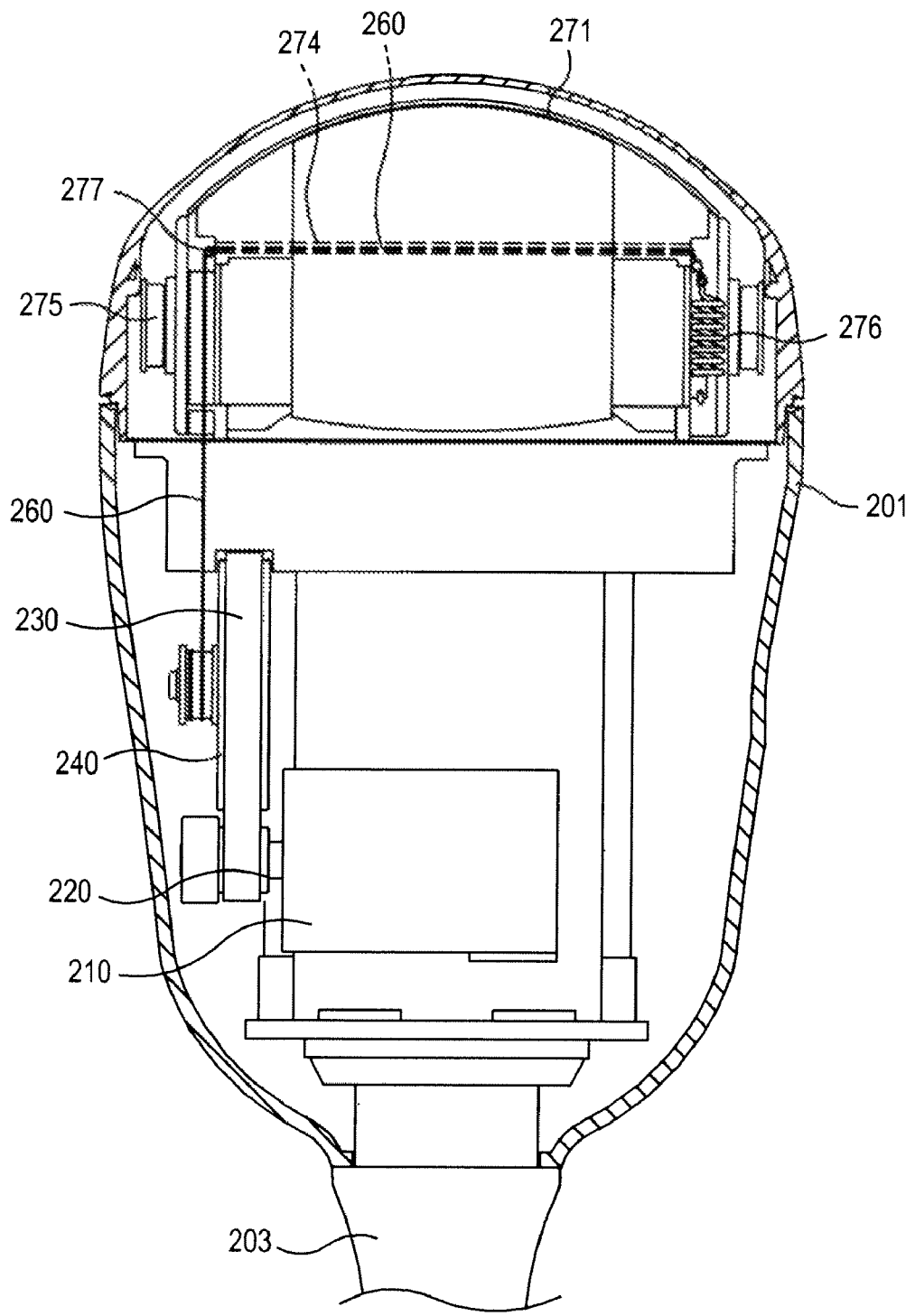
FIG. 9 is a cross-sectional view of an ultrasonic probe for three-dimensional imaging, which is constructed in accordance with an embodiment of the present invention.

In this embodiment shown in FIGS. 7 to 9, pin guides 277 are formed on the wire-rope guides 273. However, the pin guides 277 can be formed adjacent to the buffer spring 276. Bearings, pulleys or the like, which can reduce the friction force between the wire rope 260 and the edge of the wire-rope hole 274, can be used instead of the pin guides 277.

An operation of the device for rotating the transducer of an ultrasonic probe in accordance with the present invention will now be described.

As shown in FIG. 9, a driving force of the drive motor 210 rotates the drive pulley 220, while the belt 230 rotates the driven pulley 240. The rotation of the driven pulley 240 pulls one of a pair of wire-ropes 260. Thus, the drive force is converted into a tension of the wire-rope 260. Then, the tension of the wire-rope 260 is transmitted to the buffer spring 276 via the wire-rope guide 273 and the wire-rope hole 274. The tension makes the rotating momentum of the transducer around the rotating shaft 275, thereby rotating the transducer 270. The buffer spring 276 absorbs a shock produced while the tension of the wire-rope 260 is transmitted to the transducer 270.

When the drive motor 210 rotates in reverse, the driven pulley 240 pulls the other wire-rope 260. As a result, the transducer 270 rotates reversely in the similar process to that mentioned above.

Thus, the ultrasonic probe can be manufactured with a compact size, thereby removing the space occupied by the driven shaft disposed across the case 201. However, the spare area can be used for additional terminals for additional ultrasonic elements. Additional ultrasonic elements can improve the quality of a three-dimensional image obtained.

Further, the structure of the wire-rope holder 241 is not so complex to manufacture. Also, the buffer spring 276 can remove the buffering means of the wire-rope holder 241. As such, the manufacturing process can be simple and the productivity of an ultrasonic probe can be increased.

Embodiments of the present invention may provide a device for rotating a transducer of an ultrasonic probe. The device may comprise: a drive motor; a pulley rotatably driven by the drive motor; a pair of wire-ropes wounded around the pulley; a rotatable transducer having a plurality of ultrasonic elements; and a pair of buffer springs each connecting one end of the respective wire-rope and the transducer, wherein the buffer springs are attached to the transducer.

The pulley can include: a wire-rope holder protruded from the pulley concentrically, the wire rope being wound around the wire-rope holder; a via hole formed from the periphery to the center of the wire-rope holder for inserting one end of each wire-rope thereto; a screw hole formed from a surface of the pulley to the via hole; and a screw fastened in the screw holes for fixing the wire-rope inserted in the via hole.

A pressing member can be interposed between the wire-rope and the screw in the screw hole, wherein the pressing member has a larger cross-sectional area than the screw.

The transducer can include a pair of wire-rope guides mounted to both sides of the transducer for guiding the wire-ropes. The buffer springs can be mounted to the opposite side of the wire-rope guides on the transducer. A pair of wire-rope holes can be formed through the transducer for communicating each wire-rope guide and the corresponding buffer spring.

Pin guides having a cylindrical cross-section can be formed adjacent to one ends of the wire-rope holes.

Any reference in this specification to "one embodiment," "an embodiment," "example embodiment," etc., means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A device for rotating a transducer of an ultrasonic probe, comprising:
   a drive motor;
   a pulley rotatably driven by the drive motor;
   a pair of wire-ropes wound around the pulley, a first end of each of the pair of wire-ropes coupled to the pulley;
   a rotatable transducer having a plurality of ultrasonic elements, the transducer including a wire-rope guide mounted to each side of the transducer for guiding a respective one of the pair of wire-ropes; and a buffer spring mounted opposite to each wire-rope guide, each buffer spring coupled to a second end of each of the pair of wire-ropes and the transducer, wherein a pair of wire-rope holes extend through the transducer, wherein each of the wire-ropes passes through one of the pair of wire-rope holes so that the second end of each of the wire-ropes is coupled to a corresponding buffer spring, and wherein the pulley includes:

a wire-rope holder protruded from the pulley concentrically, the wire-ropes being wound around the wire-rope holder;

a via hole formed from a periphery to a center of the wire-rope holder for inserting the first end of each of the wire-ropes thereto;

a screw hole formed from a surface of the pulley to the via hole; and a screw fastened in the screw hole for fixing the first end of each of the wire-ropes inserted in the via hole.

2. The device of claim 1, wherein a pressing member is interposed between the first end of each of the wire-ropes and the screw in the screw hole, the pressing member having a larger cross-sectional area than the screw.

3. The device of claim 1, wherein pin guides having a cylindrical cross-section is formed adjacent to one ends of the wire-rope holes.

* * * * *